(12) United States Patent
Jones et al.

(10) Patent No.: US 9,153,002 B2
(45) Date of Patent: Oct. 6, 2015

(54) BAR CODE READER FOR A MEDICAL DEVICE

(76) Inventors: Alaster Jones, Saint-Sauveur (FR); Frank Grube, Biol (FR)

( * ) Notice: Subject to any disclaimer, the term of this patent is extended or adjusted under 35 U.S.C. 154(b) by 22 days.

(21) Appl. No.: 14/237,713

(22) PCT Filed: Jul. 26, 2012

(86) PCT No.: PCT/EP2012/064721
§ 371 (c)(1),
(2), (4) Date: Feb. 12, 2014

(87) PCT Pub. No.: WO2013/023892
PCT Pub. Date: Feb. 21, 2013

(65) Prior Publication Data
US 2015/0034713 A1    Feb. 5, 2015

Related U.S. Application Data

(60) Provisional application No. 61/522,714, filed on Aug. 12, 2011.

(30) Foreign Application Priority Data

Aug. 12, 2011  (EP) .................................. 11177458

(51) Int. Cl.
*G06K 7/10* (2006.01)
*G06Q 50/22* (2012.01)
(Continued)

(52) U.S. Cl.
CPC ...... *G06Q 50/22* (2013.01); *G06K 5/00* (2013.01); *G06K 7/10* (2013.01); *G06K 7/10792* (2013.01); *G06K 7/10861* (2013.01); *G06Q 50/24* (2013.01)

(58) Field of Classification Search
CPC ........................ G06Q 50/22; G06K 7/10792
USPC ............................................. 235/375; 705/2
See application file for complete search history.

(56) References Cited

U.S. PATENT DOCUMENTS 5,875,415 A      2/1999  Lieb et al.
2004/0019464 A1*  1/2004  Martucci et al. ............. 702/189
(Continued)

OTHER PUBLICATIONS

International Search Report dated Aug. 29, 2012, for International Application No. PCT/EP2012/064721.
(Continued)

*Primary Examiner* — Allyson Trail
(74) *Attorney, Agent, or Firm* — Cook Alex Ltd.

(57) ABSTRACT

A bar code reader (2) for a medical device (3) is configured to be attached to a central communication device (1) to which at least one medical device (3) is attachable. The bar code reader (2) comprises a bar code scanning device (21) for scanning a bar code (4), a processing device (22) for decoding the scanned bar code (4) to obtain decoded bar code data which is contained in the scanned bar code (4), and a connection line (24) for outputting the decoded bar code data to the central communication device (1). The processing device (22) herein is operative to decode bar codes (4) of different bar code types. Furthermore, the processing device (22) is configured to map the decoded bar code data to a predefined standardized output format and to output the decoded bar code data in the predefined standardized output format via the connection line (24). Thus, a bar code reader and a method for processing a bar code scanned by a bar code reader are provided which are capable of reading and interpreting bar codes of a variety of different types and allow for outputting the data contained in a bar code in a manner such that a central communication device to which the bar code reader is attached may easily interpret the data.

14 Claims, 9 Drawing Sheets

(51) Int. Cl.
*G06K 5/00* (2006.01)
*G06Q 50/24* (2012.01)

(56) References Cited

U.S. PATENT DOCUMENTS

| | | | |
|---|---|---|---|
| 2005/0032151 A1* | 2/2005 | Eisenberg et al. | 435/51 |
| 2005/0055242 A1* | 3/2005 | Bello et al. | 705/2 |
| 2006/0267753 A1* | 11/2006 | Hussey et al. | 340/505 |
| 2008/0164305 A1 | 7/2008 | Ball | |
| 2008/0208236 A1* | 8/2008 | Hobbs et al. | 606/186 |
| 2009/0144079 A1* | 6/2009 | Haider et al. | 705/2 |
| 2009/0171289 A1* | 7/2009 | Davis et al. | 604/131 |
| 2010/0025470 A1 | 2/2010 | Nakagawa | |
| 2010/0100037 A1* | 4/2010 | Cozmi et al. | 604/67 |
| 2011/0023343 A1* | 2/2011 | Turner et al. | 40/662 |
| 2011/0024491 A1* | 2/2011 | Jamali et al. | 235/375 |
| 2015/0094136 A1* | 4/2015 | Gagner et al. | 463/25 |

OTHER PUBLICATIONS

Written Opinion of the International Searching Authority dated Aug. 29, 2012, for International Application No. PCT/EP2012/064721.
International Preliminary Report on Patentability dated Nov. 14, 2013, for International Application No. PCT/EP2012/064721.

* cited by examiner

FIG 5A

Patient Identification

```
<?xml version="1.0" encoding="UTF-16"?>
```

| | | | Data Dictionary | [DATA] | Type | | Length | |
|---|---|---|---|---|---|---|---|---|
| <SPID> | | | | | | | | |
| | <VER> | [DATA] | </VER> | | | Alphanumeric | Variable | 3 |
| | <PID> | | | | | | | |
| | | <PII> | | | | | | |
| | | | <PatientID> | [DATA] | </PatientID> | Patient ID or Medical Record number | Alphanumeric | Variable | 48 MAX |
| | | | <DateOfBirth> | [DATA] | </DateOfBirth> | Date of birth | Alphanumeric | Variable | 8 MAX 12 |
| | | | <Source> | [DATA] | </Source> | Barcode info source ID | Alphanumeric | Variable | 3 |
| | | | <Gender> | [DATA] | </Gender> | | Alpha | Variable | 20 |
| | | | <IssuingEntityID> | [DATA] | </IssuingEntityID> | | Alphanumeric | Variable | 20 |
| | | | <VisitNumber> | [DATA] | </VisitNumber> | | Alphanumeric | Variable | 15 |
| | | | <AdminVisitDate> | [DATA] | </AdminVisitDate> | YYYYMMDD | Alphanumeric | Fixed | 8 |
| | | | <LastName> | [DATA] | </LastName> | | Alphanumeric | Variable | 50 |
| | | | <FirstName> | [DATA] | </FirstName> | | Alphanumeric | Variable | 30 |
| | | | <MiddleInitial> | [DATA] | </MiddleInitial> | | Alphanumeric | Fixed | 1 |
| | | | <Age> | [DATA] | </Age> | | Numeric | 9999,9999 | 9 |
| | | | <AgeUnits> | [DATA] | </AgeUnits> | | Alphanumeric | Variable | 8 |
| | | | <IssuingEntityCode> | [DATA] | </IssuingEntityCode> | | Alphanumeric | Fixed | 1 |
| | | </PII> | | | | | | |
| | | <PHY> | | | | | | |
| | | | <PhysicianID> | [DATA] | </PhysicianID> | | Alphanumeric | Variable | 15 |
| | | | <LastName> | [DATA] | </LastName> | | Alphanumeric | Variable | 50 |
| | | | <FirstName> | [DATA] | </FirstName> | | Alphanumeric | Variable | 30 |
| | | | <MiddleInitial> | [DATA] | </MiddleInitial> | | Alphanumeric | Fixed | 1 |
| | | </PHY> | | | | | | |
| | | <PVD> | | | | | | |
| | | | <MeasurementTypeCode> | [DATA] | </MeasurementTypeCode> | | Alpha | Variable | 8 |
| | | | <MeasurementUnits> | [DATA] | </MeasurementUnits> | | Numeric | 9999,9999 | 9 |
| | | | <MeasurementUOM> | [DATA] | </MeasurementUOM> | | Alphanumeric | Variable | 8 |
| | | | <MeasurementDate> | [DATA] | </MeasurementDate> | | Numeric | YYYYMMDD | 8 |
| | | | <MeasurementTime> | [DATA] | </MeasurementTime> | | Numeric | HHMM{SS} | 4 or 6 |
| | | </PVD> | | | | | | |
| | </PID> | | | | | | | |
| | <CRC32> | [DATA] | </CRC32> | | HEX value | Alphanumeric | Fixed | 8 |
| </SPID> | | | | | | | | |

FIG 5B

Employee Identification
`<?xml version="1.0" encoding="UTF-16"?>`

| | | | Data Dictionary [DATA] | Type | | Length |
|---|---|---|---|---|---|---|
| `<SEID>` | | | | | | |
| | `<VER>` [DATA] `</VER>` | | | Alphanumeric | Variable | 3 |
| | `<EID>` | | | | | |
| | | `<EII>` | | | | |
| | | `<IssuingEntityID>` [DATA] `</IssuingEntityID>` | | Alphanumeric | Variable | 20 |
| | | `<EmployeeID>` [DATA] `</EmployeeID>` | | Alphanumeric | Variable | 15 |
| | | `<BadgeNumber>` [DATA] `</BadgeNumber>` | | Alphanumeric | Variable | 15 |
| | | `</EII>` | | | | |
| | | `<EI2>` | | | | |
| | | `<LastName>` [DATA] `</LastName>` | | Alphanumeric | Variable | 50 |
| | | `<FirstName>` [DATA] `</FirstName>` | | Alphanumeric | Variable | 30 |
| | | `<MiddleInitial>` [DATA] `</MiddleInitial>` | | Alphanumeric | Fixed | 1 |
| | | `</EI2>` | | | | |
| | `</EID>` | | | | | |
| `<CRC32>` [DATA] `</CRC32>` | | | HEX value | Alphanumeric | Fixed | 8 |
| `</SEID>` | | | | | | |

FIG 5C

Drug Identification

```
<?xml version="1.0" encoding="UTF-16"?>
```

| | | | Data Dictionary [DATA] | Type | Length |
|---|---|---|---|---|---|
| <SDID> | | | | | |
| | <VER> | [DATA] | Alphanumeric | Variable | 3 |
| | </VER> | | | | |
| | <DIA> | | | | |
| | | <UDI> [DATA] </UDI> | Numeric | Variable | 48 |
| | | <DrugAlias> [DATA] </DrugAlias> | Alphanumeric | Variable | 48 |
| | | <DrugName> [DATA] </DrugName> | Alphanumeric | Variable | 48 |
| | | <StrengthAmount> [DATA] </StrengthAmount> | Numeric | 1000000 | 11 |
| | | <StrengthAmountUnitsOfMeasure> [DATA] </StrengthAmountUnitsOfMeasure> | Alpha | Variable | 8 |
| | | <CarrierAmount> [DATA] </CarrierAmount> | Numeric | 1000000 | 11 |
| | | <CarrierAmountUnitsOfMeasure> [DATA] </CarrierAmountUnitsOfMeasure> | Alpha | Variable | 8 |
| | | <UnitDoseIndicator> [DATA] </UnitDoseIndicator> | Numeric | Fixed | 1 |
| | | <LotNumber> [DATA] </LotNumber> | Alphanumeric | Variable | 48 |
| | | <ExpirationDate> [DATA] </ExpirationDate> | Alphanumeric | YYYYMM(DD) | 6 or 8 |
| | | <DoseForm> [DATA] </DoseForm> | Alphanumeric | Variable | 15 |
| | | <DoseRoute> [DATA] </DoseRoute> | Alphanumeric | Variable | 20 |
| | | <GenericEquivalenceNumber> [DATA] </GenericEquivalenceNumber> | Alphanumeric | Variable | 48 |
| | | <GenericEquivalenceSource> [DATA] </GenericEquivalenceSource> | Alphanumeric | Variable | 48 |
| | | <PackageType> [DATA] </PackageType> | Alphanumeric | Variable | 20 |
| | | <PackageCount> [DATA] </PackageCount> | Numeric | Variable | 20 |
| | | <ProtocolNumber> [DATA] </ProtocolNumber> | Alphanumeric | Variable | 20 |
| | | <ContainerID> [DATA] </ContainerID> | Alphanumeric | Variable | 48 |
| | </DIA> | | | | |
| | <PII> | | | | |
| | | <PatientID> [DATA] </PatientID> | Alphanumeric | Variable | 48 MAX |
| | | <DateOfBirth> [DATA] </DateOfBirth> | Alphanumeric | Variable | 8 MAX 12 |
| | | <Source> [DATA] </Source> | Alphanumeric | Variable | 3 |
| | | <Gender> [DATA] </Gender> | Alpha | Variable | 20 |
| | | <IssuingEntityID> [DATA] </IssuingEntityID> | Alphanumeric | Variable | 20 |
| | | <VisitNumber> [DATA] </VisitNumber> | Alphanumeric | Variable | 15 |
| | | <AdminVisitDate> [DATA] </AdminVisitDate> | Alphanumeric | YYYYMMDD | 8 |
| | | <LastName> [DATA] </LastName> | Alphanumeric | Variable | 50 |
| | | <FirstName> [DATA] </FirstName> | Alphanumeric | Variable | 30 |
| | | <MiddleInitial> [DATA] </MiddleInitial> | Alphanumeric | Fixed | 1 |
| | | <Age> [DATA] </Age> | Numeric | 9999.9999 | 9 |
| | | <AgeUnits> [DATA] </AgeUnits> | Alphanumeric | Variable | 8 |
| | | <IssuingEntityCode> [DATA] </IssuingEntityCode> | Alphanumeric | Fixed | 1 |
| | </PII> | | | | |
| | <FVID> | | | | |
| | | <SWID> [DATA] </SWID> | TBD | TBD | TBD |
| | </FVID> | | | | |
| | <CRC32> [DATA] </CRC32> | | Alphanumeric | Fixed | 8 |
| </SDID> | | | | | |

FIG 5D

Device Identification
`<?xml version="1.0" encoding="UTF-16"?>`

| | | | Data Dictionary [DATA] | Type | Length |
|---|---|---|---|---|---|
| `<Device>` | | | | | |
| | `<VER>` | | | | |
| | `<DEV>` | [DATA] | Alphanumeric | Variable | 3 |
| | | `</VER>` | | | |
| | | `<DevicetypeCode>` [DATA] `</DevicetypeCode>` | Alphanumeric | Fixed | 3 |
| | | `<Manufacturer>` [DATA] `</Manufacturer>` | Alphanumeric | Variable | 48 |
| | | `<ModelNumber>` [DATA] `</ModelNumber>` | Alphanumeric | Variable | 48 |
| | | `<SerialNumber>` [DATA] `</SerialNumber>` | Alphanumeric | Variable | 48 |
| | | `<MfgDate>` [DATA] `</MfgDate>` | Numeric | YYYYMMDD | 8 |
| | `</DEV>` | | | | |
| | `<DFI>` | | | | |
| | | `<FirmwareVersion>` [DATA] `</FirmwareVersion>` | Alphanumeric | Variable | 20 |
| | | `<FirwareDate>` [DATA] `</FirwareDate>` | Numeric | YYYYMMDD | 8 |
| | | `<OSVersion>` [DATA] `</OSVersion>` | Alphanumeric | Variable | 20 |
| | | `<OSDate>` [DATA] `</OSDate>` | Numeric | YYYYMMDD | 8 |
| | | `<BootFirmwareVersion>` [DATA] `</BootFirmwareVersion>` | Alphanumeric | Variable | 20 |
| | | `<BootFirmwareDate>` [DATA] `</BootFirmwareDate>` | Numeric | YYYYMMDD | 8 |
| | `</DFI>` | | | | |
| | `<CRC32>` [DATA] `</CRC32>` | | Alphanumeric | Fixed | 8 |
| `</Device>` | | | | | |

FIG 5E

```
Error Condition
<?xml version="1.0" encoding="UTF-16"?>

<Error>
        <Code>      [DATA]
        <Msg>       [DATA]
        </Code>
        </Msg>
</Error>
```

| Data Dictionary [DATA] | Type | Length |
|---|---|---|
| Numeric | Variable | 8 |
| Alphanumeric | Variable | 48 |

BAR CODE READER FOR A MEDICAL DEVICE

CROSS-REFERENCE TO RELATED APPLICATIONS

This is a U.S. national stage application of International Patent Application No. PCT/EP2012/064721, filed Jul. 26, 2012, which claims the benefit of U.S. Provisional Patent Application Ser. No. 61/522,714, filed Aug. 12, 2011.

The invention relates to a bar code reader for a medical device according to the preamble of claim 1 and a method of processing a bar code scanned by a bar code reader for a medical device.

A bar code reader of this kind is configured to be attached to a central communication device to which at least one medical device such as an infusion pump for administering a drug to a patient is attachable. The bar code reader comprises a bar code scanning device for scanning a bar code, a processing device for decoding the scanned bar code to obtain decoded bar code data which is contained in the scanned bar code and a connection line for outputting the decoded bar code data to the central communication device. The processing device of the bar code reader herein is operative to decode bar codes of different bar code types, such that the bar code reader is not limited to one specific bar code type, but may read and process bar codes of different shape and structure.

An arrangement of a central communication device (also denoted as rack) connected with a bar code reader and one or multiple medical devices such as infusion pumps is typically placed at a bed side of a patient in a hospital environment. The central communication device herein provides an interface for connecting several medical devices to each other and possibly via for example an Ethernet/local area network (LAN) connection to a hospital communication network and, via the network, to a hospital management system. The central communication device may also supply the medical devices—such as infusion pumps for administering different medications to a patient—with electric power.

Within the arrangement of the central communication device and the attached medical devices the bar code reader serves for example to identify a patient by scanning a bar code on a wristband of the patient, to identify a drug to be administered by scanning a label on a container containing the drug, to identify an employee of the hospital for authorization to administer the drug and/or to identify the medical device to be used by scanning a bar code on a device label. The bar code reader herein is constituted to scan and process different types of bar codes, which may occur for example on different medication containers from different suppliers or different medical devices from different manufacturers.

Commonly, the bar code reader scans a bar code and outputs the information contained in the bar code to the central communication device. The bar code reader herein does not cross-reference the information, but merely decodes the bar codes it has scanned to obtain the bar code data which is contained in the scanned bar code and to output the data to the central communication device.

If a bar code reader—in particular in case it fixedly is integrated into a medical device—reads a bar code of an unknown type, the information cannot be interpreted within the medical device. To overcome this problem, a software update of the medical device is necessary, or another bar code must be used thus changing the strategy in the types of bar-codes labels and data structures used.

From WO 2010/135189 A2 a network system with a plurality of network devices using various connection protocols is known. Within the network system a bar code reader is connected and networked with several devices and also the internet. A device manager is configured to communicate with local client terminals using different kinds of formats including for example text, numerical lists, XML, HTML or others.

It is an object of the instant invention to provide a bar code reader and a method for processing a bar code scanned by a bar code reader which are capable of reading and interpreting bar codes of a variety of different types and allow for outputting the data contained in a bar code in a manner such that a central communication device to which the bar code reader is attached may easily interpret the data.

This object is achieved with a bar code reader comprising the features of claim 1.

Accordingly, within the bar code reader the processing device is configured to map the decoded bar code data to a predefined standardized output format and to output the decoded bar code data in the predefined standardized output format via the connection line.

The instant invention makes use of the idea to map the data that has been obtained from a bar code to a predefined standardized output format already within the bar code reader. Thus, the bar code reader processes the data it decodes from a bar code to map the data with the predefined format such that the bar code reader may identify what information is provided in the bar code and what information is not. The output to the central communication device then takes place in the standardized output format such that the central communication device receives data from the bar code reader in always the same standardized format.

Hence, the central communication device will easily be able to interpret the data that it receives from the bar code reader, since the central communication device beforehand knows in what format it will receive the data from the bar code reader. The central communication device thus independent from the bar code type that has been read by the bar code reader receives the information in the predefined standardized format such that the further processing of the information within the central communication device is easy and computationally inexpensive.

With the instant invention, hence, a processing step is shifted to the bar code reader in that the bar code reader performs a mapping of the decoded bar code data to the predefined standardized output format and relieves the central communication device from the necessity of interpreting a non-standardized output.

The standardized output format may be for example the XML (Extensible Mark-up Language) format, wherein in principle also other standardized formats are conceivable. The XML format represents a set of rules for encoding documents in machine-readable form. The XML format is a textual data format based on Unicode and is widely used nowadays for the representation of arbitrary data structures.

The processing device may in one embodiment be constituted to map the decoded bar code data to predefined fields of information of the standardized output format. These fields of information may correspond to so-called XML elements representing a logical component of an XML scheme started with an XML start tag (a so-called mark-up construct) and ended with an XML end tag and containing a content between the start tag and the end tag, as it is commonly known within XML. The XML elements may for example refer to specific information of a patient, an employee, a drug or a device the bar code refers to.

The scanned bar code may contain patient identification information to identify a patient, employee identification information to identify an operator for operating a medical device, drug identification information for identifying a drug to be administered via a medical device, or device identification information to identify a specific medical device. Accordingly, using the bar code reader to scan a bar code on a label attached to the wristband of a patient the patient may be identified and further information regarding the patient and contained in the bar code may be obtained and mapped to information fields (XML elements) of the standardized output format. Similarly, an employee may be identified by scanning a bar code on a label of a wristband or a badge of an employee of a hospital, a drug may be identified by scanning a bar code on a label of a medication container, or a device such as an infusion pump that shall be used to administer the drug contained in the medication container may be identified by scanning a bar code on a label of the device.

Preferably, the bar code reader is constituted to scan and process bar codes which comply with the HIBC standard (Health Industry Bar Code standard), which is provided and set by the Health Industry Communication Council (HIBCC), in particular the standard ANSI/HIBC 3.1-2010 POSITIVE IDENTIFICATION FOR PATIENT SAFETY, currently at revision 3.1 and downloadable at http://www.hibcc.org/AU-TOIDUPN/standards.htm. Within the HIBC standard of the HIBCC data formats of bar codes used within a medical environment are defined to allow for an automatic capture of information to positively identify for example employee badges, patient wristbands, non-IV medications, IV-medications and medical devices such as infusion pumps. The data format of the bar code as defined by the HIBC standard is different than the XML format. A variety of information according to the HIBC standard may be contained in a bar code, referring for example also to administering information such as a medication dose or a drip or flow rate or the like.

For this, the processing device of the bar code reader may also be configurable to force the decoded bar code data of the scanned bar code to be correctly mapped to the format defined by the HIBC standard.

Although the bar code reader preferably is configured to scan bar codes adhering to the HIBC standard, the bar code reader possibly may also be capable of reading bar codes of other standards, for example the GS1 standard. For this, the bar code reader may be programmable to configure the processing device of the bar code reader to map the decoded bar code data of bar codes that do not conform to the HIBC standard to the predefined standardized output format.

In general, the bar code reader may be programmable (by performing a software update of the bar code reader) or configurable (by changing the configuration of the bar code reader, i.e. without updating the software but by merely adapting the settings) to enable the bar code reader to read and interpret bar codes of different label types and data structures. In each case a software update or a change in configuration is applied only to the bar code reader, such that a medical device or the central communication device does not require a software upgrade or modification to the configuration.

Because the processing device maps the decoded bar code data to the predefined standardized output format and outputs the decoded bar code data in this predefined standardized output format, the bar code reader may perform a check (for example a cyclic redundancy check, brief: CRC) to determine for example whether the scanned bar code conforms to a valid bar code type that can be read and interpreted by the bar code scanner or whether the scanned bar code contains all information corresponding to predefined fields of information that beforehand have been defined as essential. If the processing device of the bar code reader, during this check, detects an error (for example because the bar code type cannot be identified or because essential information is missing within the barcode, for example a patient identification number (patient ID) on a patient wristband), the processing device may cause the bar code reader to produce an alert such as a visible, audible or a vibrating signal. For example, if an error is detected, the bar code reader may exhibit a blinking light or may sound an alarm noise or may begin to vibrate.

In addition, the processing device may produce an error message and output this error message via the connection line to the central communication device such that the error message can be displayed on the central communication device or transmitted to a medical device such as an infusion pump and be displayed on a display of the medical device. For this, the error message advantageously at least comprises a textual part which may be read by a human, such that the cause of error may be identified and countermeasures may be taken to overcome the error.

As mentioned previously, the bar code reader is configured to read in different kinds of bar codes. The bar code herein may be of a linear bar code type, as for example defined by the CODE128 standard, or a two-dimensional bar code type, as defined for example in the PDF417 standard, the Data Matrix standard or the Aztec standard, wherein this list of standards shall not be understood to be exclusive. Rather, also bar codes of other bar code types may be read and interpreted by the bar code reader.

The bar code reader is to be attached to a central communication device which receives the output data in the standardized output format from the bar code reader.

The bar code reader herein may for example be attached to the central communication device via a releasable connection such as a USB connection providing a fast communication between the bar code reader and the central communication device and at the same time supplying electric power to the bar code reader.

The object of the invention is also achieved by a method of processing a bar code scanned by a bar code reader for a medical device, wherein the bar code reader is configured to be attached to a central communication device to which at least one medical device is attachable. The method comprises the steps of:
scanning a bar code using a bar code scanning device of the barcode reader,
decoding the scanned bar code using a processing device of the bar code reader to obtain decoded bar code data which is contained in the scanned bar code, wherein the processing device is operative to decode bar codes of different bar code types, and
outputting the decoded bar code data to the central communication device via a connection line of the bar code reader.

The processing device herein maps the decoded bar code data to a predefined standardized output format and outputs the decoded bar code data in the predefined standardized output format via the connection line.

The embodiments and modifications as described above for the bar code reader do also apply to this method.

The idea underlying the invention shall subsequently be described in more detail with reference to the embodiments of the figures. Herein, FIG. 1 shows a schematic overview of an arrangement of a central communication device connected with a number of medical devices such as infusion pumps and a bar code reader;

FIG. 5A shows an XML scheme referring to a patient identification;

FIG. 5B shows an XML scheme referring to an employee identification;

FIG. 5C shows an XML scheme referring to a drug identification;

FIG. 5D shows an XML scheme referring to a device identification; and

FIG. 5E shows an XML scheme referring to an error condition.

Figure 1:
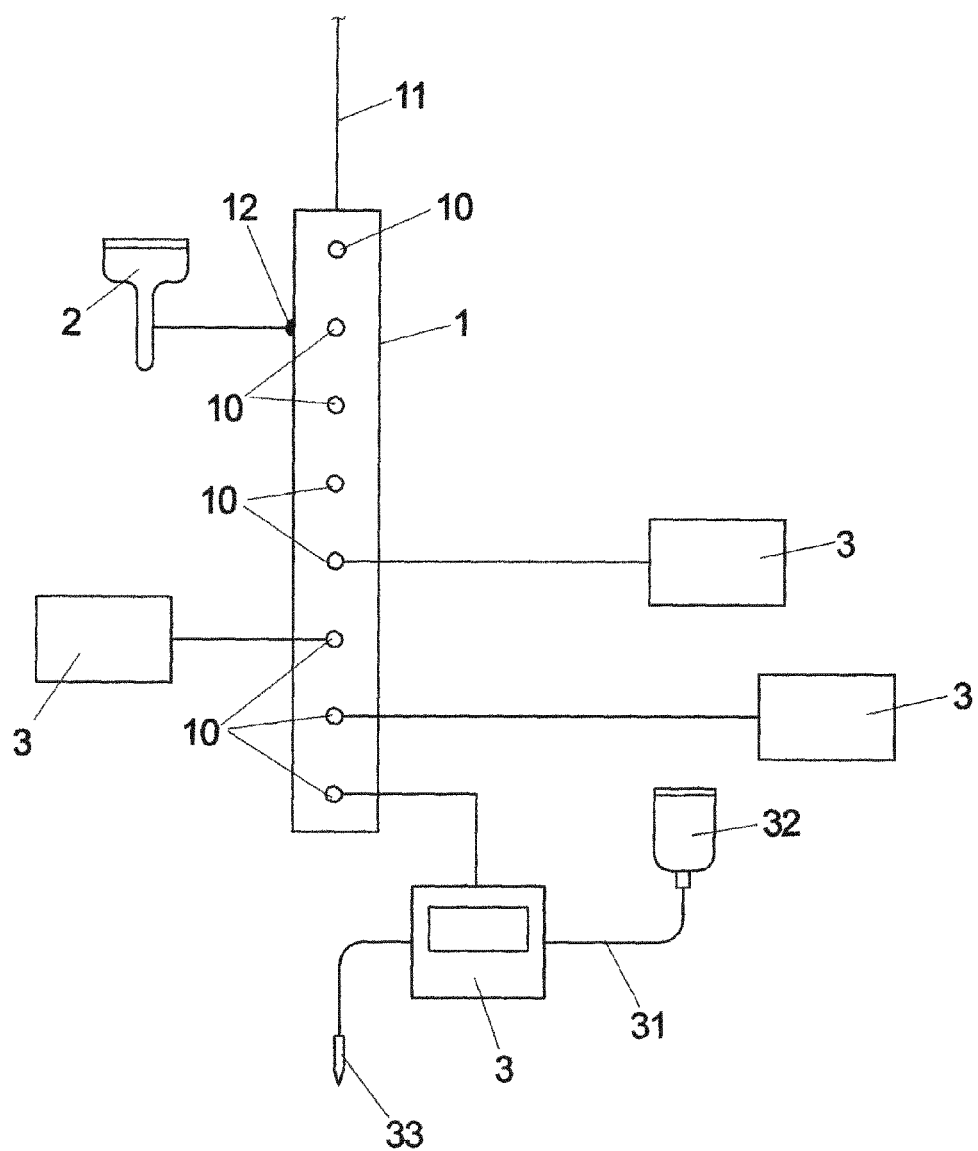
FIG. 1 shows a general arrangement of a central communication device 1 which functions as a communication spine to connect a number of medical devices 3 such as infusion pumps for administering a medication to a patient with each other and with a hospital management system.

The central communication device 1, for this purpose, comprises for example eight connectors 10 to which medical devices 3 may be attached, wherein the central communication device 1 may also mechanically hold the medical devices 3 and, thus, may serve as a rack for forming a compact, organized arrangement of the medical devices 3. The central communication device 1 further comprises a communication link 11 such as an Ethernet/local area network connection (LAN) or wireless local area network (WLAN) connection to embed the central communication device 1 with its attached medical devices 3 into a hospital network and a hospital management system.

The central communication device 1 further comprises a connection 12 such as an USB connection to which a bar code reader 2 can be attached in a releasable fashion.

Figure 2:
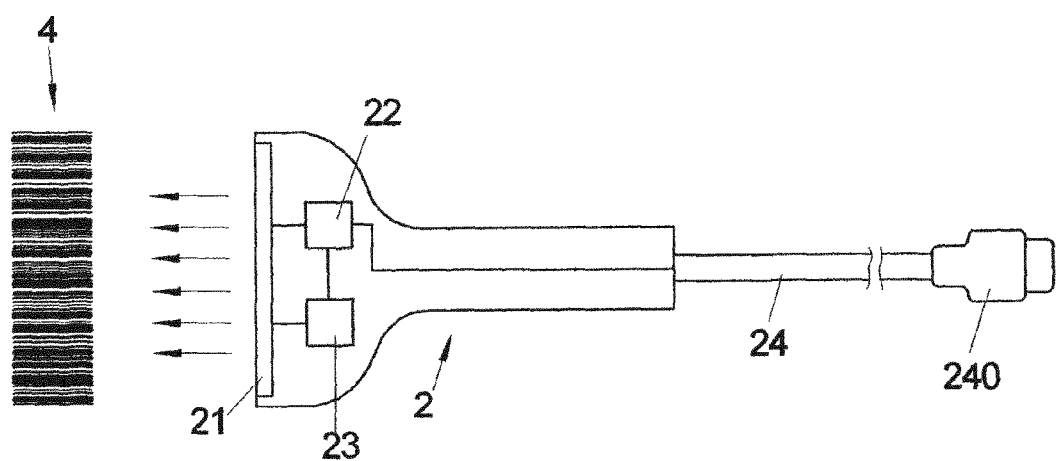
FIG. 2 shows in a schematic drawing a bar code reader.

The bar code reader 2 serves in particular to identify a patient to which a drug shall be administered, to identify an employee who is to administer the drug, to identify the drug and to identify the medical device 3 to be used to administer the drug. For this, the bar code reader 2, as shown schematically in FIG. 2, comprises a bar code scanning device 21 (possibly in the shape of a laser scanner or a camera or the like) to scan a bar code 4. The bar code scanning device 21 is connected to a processing device 22 of the bar code reader 2 and a memory device 23 for processing and storing a scanned bar code and data contained therein. The processing device 22 is connected via a connection line 24 and a connector 240 such as a USB connector to the central communication device 1 and, via the connection line 24, communicates with the central communication device 1.

The processing device 22 may for example be a microcomputer, provided on an integrated semiconductor chip.

The bar code reader 2 contains the bar code scanning device 21, the processing device 22 and the storing device 23 in a compact housing and, thus, provides a compact, handheld bar code reading device. The bar code reader 2 may be power supplied via the connection line 24, which also may provide a two-way communication link such that the bar code reader 2 may provide output data to the central communication device 1 and may receive data from the central communication device 1 for example to configure the bar code reader 2.

The bar code reader 2 is configured to scan bar codes 4 of different types. Preferably, herein the bar codes 4 conform to the HIBC standard. However, also bar codes 4 not conforming to the HIBC standard may be read by the bar code reader 2, possibly by configuring the bar code reader 2 beforehand to be able to read and interpret such bar codes 4.

The bar codes 4 to be read by the bar code reader 2 may for example have a linear or a two-dimensional structure. The bar codes 4 may be for example in the CODE128 format (linear), the Aztec format, the Data Matrix format or the PDF417 format (two-dimensional), wherein the bar code reader 2 may be operative to read and process also other bar code formats.

Figure 4A:
FIG. 4A shows an example of a bar code according to the CODE128 standard.
Figure 4A:
Figure 4B:
FIG. 4B shows an example of a bar code according to the Aztec standard.
Figure 4B:
Figure 4C:
FIG. 4C shows an example of a bar code according to the Data Matrix standard.
Figure 4C:
Figure 4D:
FIG. 4D shows an example of a bar code according to the PDF417 standard.
Figure 4D:

Examples of different bar codes 4 are shown in FIG. 4A to 4D. Each bar code 4 herein contains the information identifying a female patient with identification number MRN445414 and born on Dec. 14, 1956, obtained from a patient wristband issued by Massachusetts General Hospital (MGH) for visit number 01234572, the patient having been admitted on Dec. 12, 2004. The patient name is Ima N. Otwell. The bar code 4 according to FIG. 4A herein represents the information in the CODE128 linear format. The bar code 4 according to FIG. 4B corresponds to the Aztec format. The bar code 4 according to FIG. 4C corresponds to the Data Matrix format. And the bar code 4 according to FIG. 4D is in the PDF417 format.

As can bee seen from FIG. 4A to 4D, the bar code 4 according to the CODE128 linear format requires far more space to contain the same information than the bar codes 4 with a two-dimensional structure. The CODE128 linear bar code is not applicable to include more detailed information into the bar code.

Figure 3:
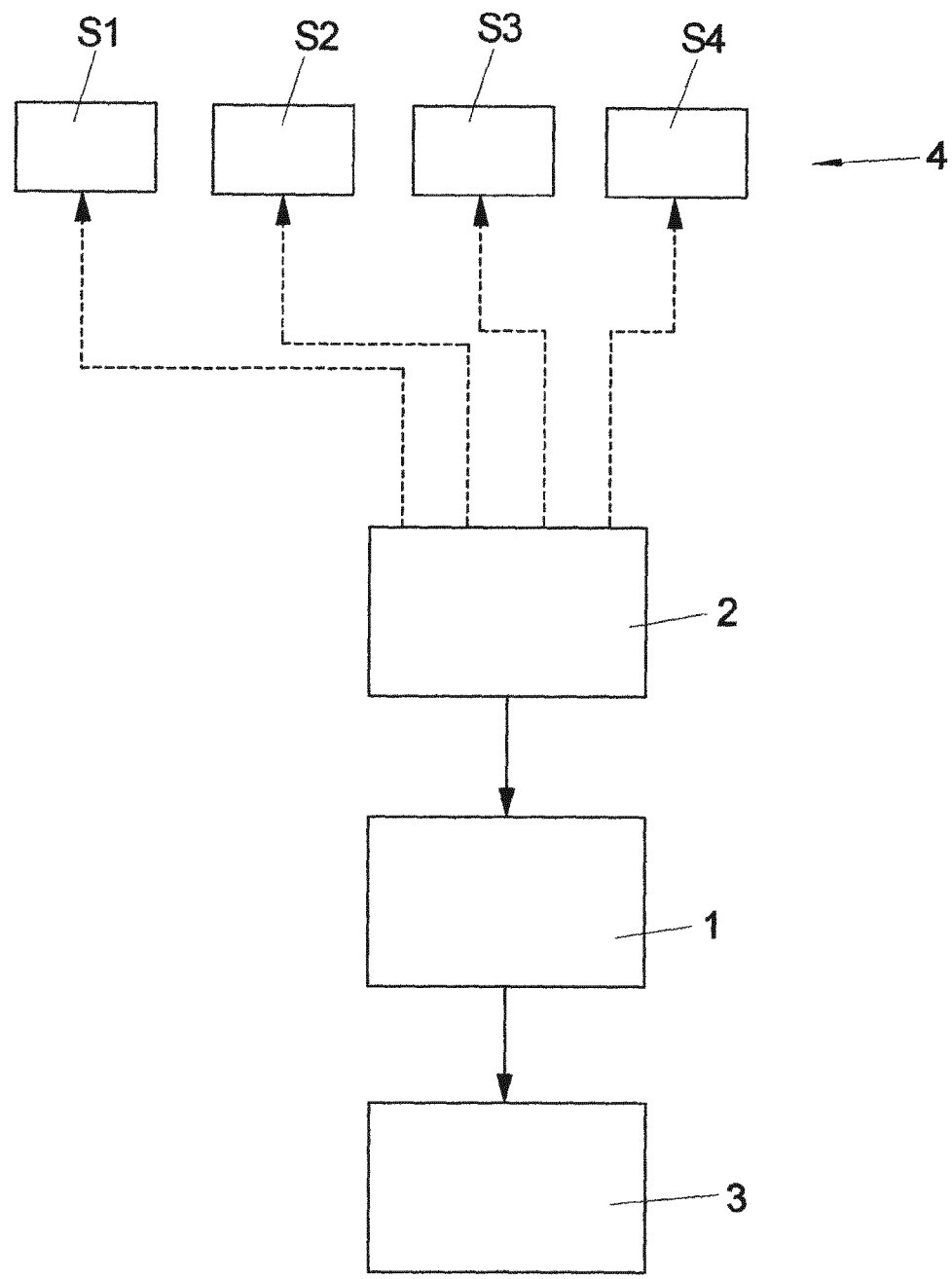
FIG. 3 shows a schematic diagram of a data flow from a bar code reader to a medical device.

The general procedure when reading a bar code 4 is illustrated in FIG. 3. Herein, the bar code reader 2 reads a bar code 4 from a drug label 51 on a drug container, a patient ID label 52 of a patient's wristband, an employee ID label 53 on an employee's badge or wristband, or a device label 54 on a medical device 3. The bar code reader 2 decodes the bar code 4 it has scanned to obtain the data contained in the bar code 4. The processing device 22 then maps the decoded bar code data to a predefined standardized output format and outputs the decoded bar code data in this predefined standardized output format via the connection line 24 to the central communication device 1, which transmits the data to one or multiple medical devices 3.

The predefined standardized output format which the processing device 22 uses to map the data contained in a scanned bar code 4 may for example be the XML format. Then, by using specific predefined XML schemes relating to patient identifying information, employee identifying information, drug identifying information and/or device identifying information it is possible to map the information contained and extracted from a bar code 4 to specific fields of information (so-called XML elements) which are defined in the standardized output format beforehand and define a structure of information which the processing device 22 of the bar code reader 2 uses to communicate the data contained in a bar code 4 to the central communication device 1.

FIG. 5A to 5D show examples of different XML schemes relating to a patient identification (FIG. 5A), an employee identification (FIG. 5B), a drug identification (FIG. 5C), a device identification (FIG. 5D) and an error condition (FIG. 5E) and give examples of XML elements defining specific fields of information in a predefined XML scheme. For example, referring to FIG. 5A, patient information may be described by XML elements relating for example to a patient identification number, a date of birth, a gender, a last name or a first name. Each XML element is started with a start tag (e.g. <PatientID>, <DateOfBirth>, <Gender>, <LastName>, <FirstName>) and is ended with an end tag (e.g. </PatientID>, </DateOfBirth>, </Gender>, </LastName>, </FirstName>) and may contain content (denoted as [DATA] in the XML schemes) in between the start tag and the end tag which carries the actual information. This format may be modified at implementation by adding or removing fields and metadata and may be derived from the (third party) bar code formats encountered during use of the bar code reader. The content of the XML elements is to be filled with the data extracted from the scanned bar code 4 to the extent of the information contained in the bar code 4. Some of the information in the XML scheme herein may be denoted as essential information that necessarily must be included in a bar code 4 for example on a patient's wristband.

The processing device 22 outputs the data extracted from a scanned bar code 4, hence, in a predefined standardized format which can easily be interpreted by the central communication device 1. This is achieved in that the processing device 22 performs a mapping between the data scanned from a bar code 4 to the predefined standardized format, namely the XML format. The output data then is provided in this XML format, such that the output data may be easily interpreted and processed further by the central communication device 1.

Referring again to FIG. 3, the bar code reader 2 after having processed and mapped the bar code data to the standardized output format outputs the data in this standardized output format to the central communication device 1, which then transmits the data to the medical device 3 such that the medical device 3 for example receives information regarding the drug to be administered to a patient, the dosage or the flow or drip rate to administer the drug.

Because the bar code reader 2 with its processing device 22 performs a mapping and thus an interpretation of the data contained in the bar code 4, it also is possible to perform a validity check of the data already in the bar code reader 2. In particular, the bar code reader 2 may check whether the bar code 4 conforms to a valid bar code type or whether all required information is contained in the bar code 4. If for some reason an error is detected, the bar code 2 may produce an audible, visible or vibrating signal to alert a user, and in addition may produce an error message and output this error message using an XML scheme as indicated in FIG. 5E to the central communication device 1, such that the central communication device 1 can transmit the error message 1 to a medical device 3. The error message preferably is in a textual, human readable form such that a user from the error message can identify the error and can act accordingly to overcome the error.

In a particular embodiment, the bar code reader 2 with its processing device 22 validates the data it reads before or after mapping. This comprises a calculation of the data validity compared to the content of the read bar code 4. For example, the bar code 4 contains data fields and at the end of each data field or at the end of all data fields is a checksum, generated by an algorithm on the labelling system. The bar code reader 2 reads the barcode and maps the data and checksum(s) to the corresponding fields. It then calculates the checksum from the data field and matches it to the bar code read checksum value. If the two values do not correspond, the label is rejected (by the bar code reader 2 via an audible tone, a message displayed on a display, vibration or other means). This is an additional mechanism to secure the data has been correctly generated and read. In addition, a host may perform a second pass once the mapped data has been already pre-verified by the bar code reader 2. This ensures that the scanning of the bar code 4 was good and the label is correct before or after mapping the data and before sending it to the host to re-perform this action on the mapped data.

In a further embodiment, the barcode reader 2 with its processing device 22 validates (in addition or as an alternative to the checksum validation as mentioned above) each field of data or the data fields comprising an as essential denoted information, based on it's configuration settings, to assure that the data contained within a certain field matches specific criteria (for example, minimum and maximum number of characters and/or illegal characters). This improves device functioning. For example, if a Patient ID field contained only three characters where between 10 and 12 are required, the barcode reader 2 may signal an error. Especially, in such a case the barcode reader 2 may signal a valid read but substitutes a message in the error condition XML schema explaining why the data is not valid. Alternatively or in addition, the error could be indicated and/or displayed by the central communication device (1) or a medical device (3) attached to the central communication device (1). In addition, a host may perform a second pass once the mapped data has been already pre-verified by the bar code reader 2.

The invention is not limited to the embodiments as described above, but may also be implemented in entirely different ways. In particular, possibly also other predefined standardized data formats than the XML format may be used to provide the data output of the bar code reader in a standardized form which is easily interpretable by the central communication device.

LIST OF REFERENCE NUMERALS

1 Central communication device
10 Connector
11 Communication link
12 Connection
2 Bar code reader
21 Bar code scanning device
22 Processing device
23 Memory device
24 Connection line
240 Connector
3 Infusion pump
31 Tube
32 Infusion bag
33 Cannula
4 Bar code
51 Manufacturer's drug label
52 Third party's drug label
53 Patient ID label
54 Employee ID label
55 Device label

The invention claimed is:

1. A bar code reader for a medical device, wherein the bar code reader is configured to be attached to a central communication device to which at least one medical device is attachable, the bar code reader comprising:
 a bar code scanning device for scanning a bar code;
 a processing device for decoding the scanned bar code to obtain decoded bar code data which is contained in the scanned bar code, wherein the processing device is operative to decode bar codes of different bar code types; and
 a connection line for outputting the decoded bar code data to the central communication device, wherein the processing device is configured to map the decoded bar code data to predefined fields of information of a predefined standardized output format and to output the decoded bar code data in the predefined standardized output format via the connection line, and wherein the processing device is configured to check whether the scanned bar code contains all information corresponding to the predefined fields of information that beforehand have been defined as essential.

2. The bar code reader according to claim 1, wherein the standardized output format is XML format.

3. The bar code reader according to claim 1, wherein the processing device is configured to map the decoded bar code data to predefined fields of information of the standardized output format.

4. The bar code reader according to claim 1, wherein the scanned bar code contains at least one of:
   patient identification information to identify a patient;
   employee identification information to identify an operator for operating a medical device;
   drug identification information for identifying a drug to be administered via a medical device, and device identification information to identify a medical device.

5. The bar code reader according to claim 1, wherein the scanned bar code complies with the HIBC standard.

6. The bar code reader according to claim 1, wherein the bar code reader is programmable to configure the processing device to map the decoded bar code data to the predefined standardized output format.

7. The bar code reader according to claim 1, wherein the processing device checks whether the scanned bar code conforms to a valid bar code type.

8. The bar code reader according to claim 1, wherein the processing device is configured to check whether the information of at least one field matches specific criteria of minimum and maximum number of characters and/or illegal characters.

9. The bar code reader according to claim 7, wherein the processing device is configured to produce an alert in case an error is detected.

10. The bar code reader according to claim 7, wherein the barcode reader is configured to output an error message via the connection line to be displayed by the central communication device or a medical device attached to the central communication device in case an error is detected.

11. The bar code reader according to claim 1, wherein the bar code is of a linear bar code type or a two-dimensional bar code type.

12. The bar code reader according to claim 1, wherein the bar code type complies with CODE128 standards, PDF417standards, Data Matrixstandards or Aztec standards.

13. The bar code reader according to claim 1, wherein the connection line is releasably connectable to the central communication device.

14. A method of processing a bar code scanned by a bar code reader for a medical device, wherein the bar code reader is configured to be attached to a central communication device to which at least one medical device is attachable, the method comprising the steps of:
   scanning a bar code using a bar code scanning device of the bar code reader, decoding the scanned bar code using a processing device of the bar code reader to obtain decoded bar code data which is contained in the scanned bar code, wherein the processing device is operative to decode bar codes of different bar code types, and
   outputting the decoded bar code data to the central communication device via a connection line of the bar code reader, wherein the processing device maps the decoded bar code data to predefined fields of information of a predefined standardized output format and outputs the decoded bar code data in the predefined standardized output format via the connection line, and wherein the processing device checks whether the scanned bar code contains all information corresponding to the predefined fields of information that beforehand have been defined as essential.

* * * * *